(12) United States Patent
Leube et al.

(10) Patent No.: US 11,143,886 B2
(45) Date of Patent: Oct. 12, 2021

(54) METHOD FOR OPTIMIZING AN OPTICAL AID BY WAY OF AUTOMATIC SUBJECTIVE VISUAL PERFORMANCE MEASUREMENT

(71) Applicant: Carl Zeiss Vision International GmbH, Aalen (DE)

(72) Inventors: Alexander Leube, Aalen (DE); Christian Leibig, Munich (DE); Arne Ohlendorf, Tübingen (DE); Siegfried Wahl, Donzdorf (DE)

(73) Assignee: Carl Zeiss Vision International GmbH, Aalen (DE)

( * ) Notice: Subject to any disclaimer, the term of this patent is extended or adjusted under 35 U.S.C. 154(b) by 0 days.

(21) Appl. No.: 17/130,342

(22) Filed: Dec. 22, 2020

(65) Prior Publication Data
US 2021/0157168 A1 May 27, 2021

Related U.S. Application Data

(63) Continuation of application No. PCT/EP2019/061478, filed on May 6, 2019.

(30) Foreign Application Priority Data

Jun. 29, 2018 (EP) ..................... 18180876

(51) Int. Cl.
*G10L 15/00* (2013.01)
*G10L 15/16* (2006.01)
(Continued)

(52) U.S. Cl.
CPC ............ *G02C 7/028* (2013.01); *G02C 7/027* (2013.01); *G06F 30/27* (2020.01); *G06N 3/08* (2013.01)

(58) Field of Classification Search
CPC ......... A61B 3/0025; A61B 3/02; G02C 11/10; G02C 7/027; G02C 7/028; G06F 30/27; G06N 3/0454; G06N 3/08
(Continued)

(56) References Cited

U.S. PATENT DOCUMENTS 8,690,325 B1 * 4/2014 Straus .................. A61B 5/0002 351/200
9,594,983 B2 * 3/2017 Alattar ................. G06K 9/6259
(Continued)

FOREIGN PATENT DOCUMENTS

WO 2018022521 A1 2/2018

OTHER PUBLICATIONS

Extended European Search Report issued in EP18180876.7, to which this application claims priority, dated Feb. 12, 2019.
(Continued)

*Primary Examiner* — Khai N. Nguyen
(74) *Attorney, Agent, or Firm* — Thrive IP®; Georg M. Hasselmann (57) ABSTRACT

A method for optimizing an optical aid by way of automatic measurement of the subjective visual performance, a method for producing a correspondingly optimized optical aid, an apparatus for producing optical aids, a computer program having a program code for carrying out the optimization method, which program can be run on a processor, and a non-transitory storage medium comprising the computer program stored thereon are disclosed. The method for optimizing the optical aid includes the automatic determination of subjective visual acuity using machine learning.

18 Claims, 5 Drawing Sheets

(51) Int. Cl.
  *G10L 13/00* (2006.01)
  *G02C 7/02* (2006.01)
  *G06F 30/27* (2020.01)
  *G06N 3/08* (2006.01)

(58) Field of Classification Search
  USPC ........................................ 704/231, 232, 259
  See application file for complete search history.

(56) References Cited

U.S. PATENT DOCUMENTS

| | | | |
|---|---|---|---|
| 10,095,050 B2* | 10/2018 | Wahl | G16H 20/70 |
| 10,168,549 B2* | 1/2019 | Ohlendorf | G02C 7/081 |
| 10,298,911 B2* | 5/2019 | Shuster | H04N 13/293 |
| 10,722,180 B2* | 7/2020 | Zhang | G16H 40/63 |
| 10,902,539 B2* | 1/2021 | Rodriguez | G06K 9/627 |
| 2015/0055855 A1* | 2/2015 | Rodriguez | G06K 9/6259 |
| | | | 382/159 |
| 2015/0088870 A1* | 3/2015 | Jayasundera | G16H 50/20 |
| | | | 707/723 |
| 2017/0243317 A1* | 8/2017 | Rodriguez | G06K 9/6259 |
| 2017/0273552 A1* | 9/2017 | Leung | G06F 3/011 |
| 2017/0365101 A1* | 12/2017 | Samec | A61B 5/163 |
| 2017/0371178 A1* | 12/2017 | Crespo | G06N 20/00 |
| 2018/0136486 A1* | 5/2018 | Macnamara | A61B 3/14 |
| 2019/0110753 A1* | 4/2019 | Zhang | G16H 50/20 |
| 2021/0157168 A1* | 5/2021 | Leube | A61B 3/02 |

OTHER PUBLICATIONS

International Search Report and Written Opinion by the International Searching Authority issued in PCT/EP2019/061478, to which this application claims priority, dated May 29, 2019, and English-language translation thereof.

* cited by examiner

METHOD FOR OPTIMIZING AN OPTICAL AID BY WAY OF AUTOMATIC SUBJECTIVE VISUAL PERFORMANCE MEASUREMENT

CROSS REFERENCE TO RELATED APPLICATIONS

This application is a continuation application of International patent application PCT/EP2019/061478, filed May 6, 2019, designating the United States and claiming priority from European patent application EP 18180876.7, filed Jun. 29, 2018, and the entire content of both applications is incorporated herein by reference.

TECHNICAL FIELD

The disclosure relates to a method for optimizing an optical aid by means of automatic determination of subjective visual acuity.

BACKGROUND

Known methods for determining subjective visual acuity, for example the resolution of a person's eye, are based on the assumption that there is a connection between optical defects and the visual acuity to be expected. The known methods model the visual system by means of various optical and neural filter functions. This modeling is based on subjective test subject measurements. Subjective test subject measurements are laborious and are subject to falsification of the results due to disruptive influences, for example due to fatigue of the test subject. Furthermore, the filter functions have adjustable weightings that must be adapted appropriately. In particular, the neural transfer function may be highly non-linear and therefore difficult to describe. Neural transfer functions can vary greatly from person to person. With the known methods there is therefore no guarantee that sufficiently accurate results will be achieved. Correspondingly, the optimization of an optical aid by known methods for determining subjective visual acuity is also laborious, susceptible to disruptive influences and not sufficiently accurate.

SUMMARY

The present disclosure is based on the object of eliminating the disadvantages from the related art. In particular, a method is to be provided for optimizing an optical aid in which the subjective visual acuity is determined quickly, without disruptive influences and with good accuracy. Furthermore, a production method for a correspondingly optimized optical aid and an apparatus for producing a correspondingly optimized optical aid are to be specified.

According to the disclosure, this object is achieved with respect to the optimization method by optimizing an optical aid by the automatic determination of subjective visual acuity using machine learning, with respect to the production method by determining surface machining data according to the second parameterization of the optimized optical aid, and with respect to the apparatus by a device for determining surface machining data according to the second parameterization of the optimized optical aid. Advantageous exemplary embodiments of the disclosure are specified below.

The method according to the disclosure for optimizing an optical aid carries out an automatic determination of subjective visual acuity using machine learning and comprises the following steps:

a) providing at least one training data set,
b) training an artificial neural network by means of the at least one training data set,
c) generically creating a stimulus image,
d) parameterizing the stimulus image, a first and a second parameterization being performed, and typically the first parameterization of the stimulus image taking place by using at least an image size of the stimulus image, a stimulus contrast and/or a stimulus shape,
e) providing a recognition probability function,
f) classifying the stimulus image by the trained neural network to provide a classification of the stimulus image,
g) determining a recognition probability for the first parameterization performed in step d) on the basis of the classification of the stimulus image,
h) adapting the first parameterization of the stimulus image on the basis of the determined recognition probability,
i) classifying the adapted stimulus image by the trained neural network to provide a classification of the adapted stimulus image,
j) determining the recognition probability for the first parameterization adapted in step h) on the basis of the classification of the adapted stimulus image,
k) repeating steps h) to j) until a termination criterion is achieved with regard to finding a threshold for subjective visual acuity,
l) determining the threshold of subjective visual acuity,
m) repeatedly running through steps d) to l) with a different second parameterization in each case, the second parameterization of the stimulus image in each case comprising the application of at least one property of the optical aid to the stimulus image,
n) optimizing the optical aid by selecting the second parameterization with the highest subjective visual acuity determined in step l).

The method is an in-vitro method; that is to say, none of the method steps is carried out on or in the human body.

The method steps are typically carried out in the specified sequence a)-n).

The term "optical aid" is used in the present patent application as a collective term. The term "optical aid" comprises spectacle lenses, spectacle lens blanks, progressive lenses, contact lenses, intraocular lenses, objectives, binocular optics, and combinations of different optics. In this context, spectacle lenses are also understood to mean spectacle lens blanks and progressive lenses. The "optical aid" is typically a lens or a pair of spectacles with two lenses.

The term "optical system" is understood in the present patent application as meaning an optical aid and/or a human eye.

In the present patent application, the human eye is the eye of a certain person for whom specifically the optimization according to the disclosure of an optical aid (in particular a spectacle lens) is carried out.

The term "visual acuity" is used in the present patent application interchangeably with the term "performance" or "visual performance." The "visual acuity" or the "(visual) performance" stands for the ability of an optical and/or neural system, that is to say for the ability of the eye (together with the optic nerve and the brain) and/or an optical aid, to process and/or resolve a given stimulus image sufficiently. The "visual acuity" or "(visual) performance" depends here on the type of parameterization of the stimulus image. The "visual acuity" or "(visual) performance" refers with regard to the image size parameter to the resolution, with regard to the contrast parameter to the ability to process low or high gradations of contrasts sufficiently and with regard to the shape parameter to the ability to distinguish between shapes. The term "subjective visual acuity" refers here to the visual acuity of a person. In the case of the image size parameter, an equivalent definition of the parameter is possible by using the viewing angle corresponding to the image size. In addition, the image size or viewing angle parameter may relate to the entire stimulus image or only to the extent of a critical detail within the stimulus image. For example, a critical detail is the width of the gap in a Landolt ring.

The stimulus image is typically a Landolt C (also called a Landolt ring). This is a round C, the gap of which can have different alignments, in particular the eight different alignments "0°," "45°," "90°," "135°," "180°," "225°," "270°," or "315°". The stimulus image may alternatively be, for example, a Snellen hook (also called an E hook), a letter, a number, a contrast pattern, or a natural image. A natural image is understood as meaning in particular an image with specific distributions of viewing angles occurring that are based on a natural environment. Generally speaking, any stimulus image suitable for determining visual acuity is suitable for carrying out the disclosure. The size relationships in the alternative stimulus images are typically based on the size relationships in a Landolt ring. The stimulus image may be created synthetically.

Each stimulus image has at least one recognizable feature. With the Landolt ring for example, the feature is the alignment of the gap. With a number, the feature is the identification what number is represented.

In the context of this application, parameterization is understood as meaning the specific value or the specific values of the relevant parameter or parameters. More generally speaking, the parameterization is a specific point in a one-dimensional or multi-dimensional parameter space. If the parameter under consideration is for example the image size, the parameterization is a specific value of the image size. The image size corresponds to a viewing angle at which the stimulus image would be presented to a person (or a test subject) under standardized conditions (in particular at a fixed distance).

The training data set provided in step a) typically reflects the subjective visual acuity of a large number of real test subjects when recognizing stimulus images. To create the training data set, a stimulus image is for example presented to a first real test subject on a monitor or on a board gradually with different parameterizations, that is to say with different values of one or more parameters, for example with different values of the image size and/or the contrast. For each parameterization of the stimulus image presented to him/her, the real test subject has to communicate his/her subjective recognition or non-recognition of a feature shown on the stimulus image. This subjective response of the real test subject may take place for example by actuating a key or a button, typically a specific key for recognition and a specific other key for non-recognition. Typically, the test subject must in any case make a specific decision, that is to say for example he/she has to decide on either "recognized" or "not recognized." In the case of a Landolt ring, it is typically provided that the test subject has to decide on a specific gap alignment from the possible angles "0°," "45°," "90°," "135°," "180°," "225°," "270°," or "315°." Therefore, if necessary, the test subject has to guess. This decision required of the test subject is also referred to as the forced choice paradigm.

The procedure described for the first real test subject is carried out on a large number of other real test subjects. It is important here to ensure comparability of the data obtained in each case by using standardized conditions for data collection. The distance between the test subject and the monitor or board, the illumination and/or the exposure time are typically standardized. The individual test subjects are also typically as similar as possible. For example, all of the test subjects may be young, healthy people without defective vision and with normal neural properties. Typically, all test subjects may have defective vision. The differently parameterized stimulus images may be presented to the test subjects in each case while they are using or not using an optical aid.

The training data set may however also comprise different groups of real test subjects, for example children and adults; adults and seniors; or children, adults and seniors. In addition, the training data set may comprise different age groups, for example 30- to 40-year-olds, 40- to 50-year-olds, 50- to 60-year-olds, and 60- to 70-year-olds.

Furthermore, a number of stimulus images with different features may also be presented to each individual real test subject. For example, when the Landolt ring is used as a stimulus image, the eight different gap alignments of the C may be presented as different manifestations of a feature. The individual alignments may in each case be presented in blocks with varying parameterization or mixed as desired or presented in constant change with one another.

For example, with the large number of test subjects, altogether 100-1,000,000 presentations, typically 1,000-100,000 presentations, particularly typically 2,000 to 10,000 presentations, of a stimulus image with a certain manifestation of a feature in different parameterizations can be carried out. When presenting Landolt rings with eight different gap alignments, for example the number of presentations is multiplied by eight.

Furthermore, a number of runs may take place with each individual real test subject, with the stimulus image in each run typically having a differently manifested optical aberration, for example a different sharpness. For example, a first run may take place with a sharp stimulus image and a second run with an unsharp stimulus image. As an alternative to this, in the case of a group of real test subjects of the same type, it may be that only one run is respectively carried out for each test subject with respect to a stimulus image with different parameterizations and/or different manifestations of a feature; in this case, however, the stimulus image with a first sharpness may be provided to a first number of test subjects and the stimulus image with a second sharpness may be provided to a second number of test subjects. Optionally, the stimulus image with a third sharpness may be provided to a third number of test subjects, and so on up to the stimulus image with an nth sharpness being provided to an nth number of test subjects. For example, in the case of a group of real test subjects of the same type, some of the test subjects may be presented with a sharp stimulus image for the described determination of the subjective visual acuity and some others of the test subjects may in each case be presented with an unsharp stimulus image.

Typically, the stimulus images may be presented to each individual test subject with five to ten different degrees of sharpness. This correspondingly results for example in a total number of 4,000-80,000,000 presentations, typically 40,000-8,000,000 presentations, particularly typically 80,000-800,000 presentations for the creation of a training data set.

The training data sets provided comprise the differently parameterized stimulus images, possibly provided with different manifestations of a feature, as well as possibly information on the actual manifestations of a feature of the individual stimulus images. There is a clear assignment here between each individual stimulus image and its actual manifestation of the feature. In addition, the training data sets typically comprise the respective subjective response of the test subjects for recognizing the feature or features shown on the stimulus images. As an alternative to interrogating subjective visual acuity in real test subjects, the training data set may also be generated exclusively synthetically. In this case, the training data set therefore only comprises the differently parameterized stimulus images provided with different manifestations of a feature.

The neural network is typically made up of different layers. It may comprise an input layer, a certain number of hidden layers, and an output layer. Each layer in this case comprises a large number of neurons. The neurons of neighboring layers are in this case connected to one another while taking weights into account. The training data set is typically provided to the input layer. In particular, the individual stimulus images and, if applicable, the information about the manifestation of a feature actually contained on the individual stimulus images in each case are provided to the input layer. Furthermore, the respective subjective response of the test subjects for recognizing the feature or features shown on the stimulus images may be provided to the input layer. During the training of the neural network according to step b), in particular the weights are adjusted in such a way that a correct assignment between the individual stimulus images and the manifestations of a feature actually contained on these in each case is achieved in the output layer. The training process typically goes through a number of repetitions. A learning rate is in this case determined on the basis of the changes in the weights that occur. The number of repetitions is typically determined by means of the learning rate. The training process may be terminated for example when the learning rate reaches or undershoots a certain lower limit value. The neural network is in this case considered to be sufficiently trained.

Generic creation according to step c) means generating or selecting the stimulus image per se. A Landolt ring (or "Landolt C"), a Snellen hook (or "E hook"), a letter, a number, a contrasting pattern or a natural image may be provided for example as the stimulus image. Generic creation of the stimulus image typically comprises the provision of a feature space comprising a number of manifestations of a feature, i.e., the possibility of selecting different manifestations of a feature, for example the eight possible alignments of the gap in the Landolt ring. The feature space may be one-dimensional or multi-dimensional.

The stimulus image created generically in step c) and/or the feature space typically correspond to the stimulus image and/or feature space used in the creation of the at least one training data set. Steps a), b) and c) are typically carried out in this chronological order. As an alternative to this, it is also conceivable to select a training data set that matches the generically created stimulus image and its feature space. The training data set could for example be selected from a database of a large number of training data sets. In this case, steps a), b) and c) are therefore carried out in the chronological order c)->a)->b).

Typically, in step d) one of the manifestations of a feature is selected from the feature space and provided in the stimulus image. For example, with the Landolt ring, one of the eight possible alignments of the gap is selected as a manifestation of a feature and provided in the stimulus image. The selection and provision of the manifestation of a feature typically takes place before the parameterization of the stimulus image. The manifestation of a feature is typically selected randomly, for example on the basis of a normal distribution or uniform distribution. In the case of a multi-dimensional feature space, the manifestation of a feature may be understood as a vector. The selection and provision of the manifestation of a feature typically takes place by control software. The control software may use a psychophysical algorithm or be a psychophysical algorithm.

The parameterization according to step d) typically takes place by the control software or by the psychophysical algorithm. When parameterizing according to step d), input values (that is to say initial values) are typically defined for the control software or for the psychophysical algorithm.

The first parameterization is understood in the context of this application as a specific value or specific values of one or more relevant first parameters. The first parameter or parameters form a first parameter space. More generally speaking, the first parameterization is a specific point in the one-dimensional or multi-dimensional first parameter space. If the first parameter under consideration is for example the image size, the first parameterization is a specific value of the image size. The image size corresponds to a viewing angle resulting from it under standard conditions. The stimulus contrast is a contrast value of the stimulus image per se or the contrast value of a feature shown on the stimulus image. The stimulus contrast may be a black-and-white contrast and/or a color contrast. The stimulus shape is the specific shape of a feature shown on the stimulus image. For example, the stimulus image may comprise a circle as a feature. In this case, the first parameterization may be a sine modulated onto the circle, as a result of which the circle may be provided with bulges. The circle may be perceived by a person as a perfect circle or as deformed (or correspondingly classified by the neural network as a perfect circle or as deformed). The shape parameter may also be investigated for example by providing radial frequency patterns as stimulus images. According to the method according to the disclosure, the first parameterization may take place for example exclusively by using the image size. As an alternative to this, the first parameterization may take place exclusively by using the stimulus contrast, the stimulus images remaining unchanged in their image size. Furthermore, the first parameterization may take place exclusively by using the stimulus shape, the stimulus images remaining unchanged in their image size.

The second parameterization takes place by applying at least one property of the person's eye and/or at least one property of an optical aid (for example a spectacle lens), typically by applying an optical aberration or a number of optical aberrations of the eye and/or the optical aid (the spectacle lens) to the stimulus image. The at least one property is therefore typically at least one optical aberration. The optical aberration or the optical aberrations of the eye and/or of the optical aid may include defocus, astigmatism, coma and/or higher-order aberrations. An optical aberration can be measured for example by a refractive power of the eye and/or the optical aid in the unit of measurement of diopters (dpt). The optical aid (for example the spectacle lens) typically brings about a correction, that is to say a compensation for defective vision of the eye. An optical aberration of the eye is in this case to be compensated for by a corresponding optical aberration on the optical aid. In this case, the optical aberration of the optical aid typically has the opposite sign to that of the optical aberration of the eye. For example, the optical aberration of the eye is +1 dpt defocus and the optical aberration of the optical aid is −1 dpt defocus.

The second parameterization is understood in the context of this application as meaning a specific value or specific values of one or more relevant second parameters. The second parameter or parameters form a second parameter space. More generally speaking, the second parameterization is a specific point in the one-dimensional or multi-dimensional second parameter space. If the second parameter under consideration is for example a sharpness of the stimulus image, the second parameterization is a specific value of the sharpness of the stimulus image. In this example, the refractive power as a property of the eye and/or the optical aid (in particular the spectacle lens) corresponds to the sharpness as a second parameterization. As an alternative to this or in addition, the second parameterization may take place by using a contrast. Also in this example, for example the refractive power as a property of the eye and/or the optical aid (in particular the spectacle lens) corresponds to the contrast as a second parameterization. This example also shows that the parameter contrast can belong to the first and/or the second parameter space, depending on the configuration of the method. This statement can be generalized. In the context of this application, however, a clear distinction is made between first and second parameters: First parameters are used to determine the threshold of the subjective visual acuity, that is to say the threshold of the subjective visual acuity is determined by varying the first parameterization. The first parameterization therefore corresponds to a stimulus intensity. Second parameters express the effect of different properties of optical systems on a stimulus image.

The first and second parameterizations typically relate to different parameters, for example the first parameterization to the image size and the second parameterization to an optical aberration.

Optical aberrations can generally be wavefront errors that are present in a description of Zernike coefficients or in any other description of optical defects. These can be measured or calculated centrally or also peripherally on the eye and/or on the optical aid (in particular on the spectacle lens). In addition or as an alternative to optical aberration, the at least one property may also be at least one scotoma (complete or partial loss of sensitivity in a part of the visual field, for example due to age-related macular degeneration or diabetic retinopathy), a distortion and/or an opacity. It is also possible for one or more of these properties to be applied to the stimulus image. As a second parameterization, for example a contrast or a change in contrast corresponds to opacity, a local obscuration or a missing area in the stimulus image corresponds to a scotoma and a change in shape corresponds to a distortion.

The recognition probability function assigns a recognition probability to each first parameterization. The recognition probability function is typically a sigmoid function. The sigmoid function is also called the gooseneck function or S function because of its shape. A sigmoid function can be mathematically determined for example by accumulating Gaussian distributions.

Classifying the stimulus image (see step f) and step i)) means assigning the stimulus image to different categories. The classification of the stimulus image by the trained neural network may be for example "recognized", "not recognized" or (in the case of a Landolt ring) "0°", "45°", "90°", "135°", "180°", "225°", "270°," or "315°". The classification made by the trained neural network can be compared by the control software (typically by the psychophysical algorithm) with an actually existing manifestation of a feature, for example with the actually existing gap alignment in the case of the Landolt ring. In particular, the control software (typically the psychophysical algorithm) may determine the classification as positive in the case of "recognized" or correct determination of the alignment of the gap (in the case of a Landolt ring) and as negative in the case of "not recognized" or incorrect determination of the alignment of the gap (in the case of a Landolt ring).

If the classification is positive, the control software (typically the psychophysical algorithm) may determine the recognition probability for the first parameterization as 100% in step g). If the classification is negative, the control software (typically the psychophysical algorithm) may determine the recognition probability for the first parameterization as 0% in step g).

The recognition probability is typically determined in step g) as the value of the recognition probability function for the first parameterization performed in step d) on the basis of the classification of the stimulus image. For this purpose, the recognition probability function may be adapted to the recognition probability determined for the first parameterization (for example the 0% or 100% from the previous example) by fitting. The value assigned by the fitted recognition probability function to the first parameterization is typically used as the recognition probability for the first parameterization for the further course of the method according to the disclosure.

Typically, in step h) again one of the manifestations of a feature is selected from the feature space and provided in the stimulus image. For example, with the Landolt ring, one of the eight possible alignments of the gap is selected as a manifestation of a feature and provided in the stimulus image. The selection and provision of the manifestation of a feature typically takes place before the adaptation of the parameterization. The manifestation of a feature is typically selected randomly, for example on the basis of a normal distribution or uniform distribution. In the case of a multi-dimensional feature space, the manifestation of a feature may be understood as a vector.

The adaptation of the first parameterization of the stimulus image in step h) typically takes place by the control software (in particular by the psychophysical algorithm) on the basis of the recognition probability determined in step g) or in step j). The adaptation of the first parameterization of the stimulus image may in this case typically take place on the basis of the recognition probability function fitted by means of the determined recognition probability. Therefore, in the following, the term "recognition probability" may refer both to the recognition probability determined in step g) or in step j) and to the value of the fitted recognition probability function for the relevant first parameterization. With a recognition probability of over 50% (or of at least 50%), the first parameterization is typically adapted in such a way that recognition of the stimulus image with the new first parameterization becomes more difficult, for example the image size is therefore reduced. Correspondingly, with a recognition probability of below 50%, the first parameterization may be adapted in such a way that recognition of the stimulus image with the new first parameterization becomes easier, for example the image size is therefore increased. The amount of the difference between the new first parameterization and the previous first parameterization is typically also dependent on the recognition probability. The amount of this difference is typically all the smaller, the closer the recognition probability is to 50%. The aim of adapting the first parameterization of the stimulus image is to bring the first parameterization close to the visual threshold.

Depending on the type of psychophysical algorithm typically used, it may be provided that, when adapting the first parameterization in step h), a first parameterization that was not previously set is always set, or that an already previously used first parameterization is set again in step h). Correspondingly, depending on the type of psychophysical algorithm, a certain first parameterization may be inquired only once or a number of times. "An inquiry" is understood here as meaning running through steps f) and g) or steps i) and j).

In step j), the control software (in particular the psychophysical algorithm) typically determines the recognition probability for the first parameterization adapted in step h) on the basis of the classification from step i). With a positive classification, the control software (typically the psychophysical algorithm) may in this case determine the recognition probability for the adapted first parameterization as 100%, provided that the relevant first parameterization was inquired for the first time, or for example an average value of 100% and the recognition probability already determined in a previous run in step j) or already in step g) for the same first parameterization, provided that the relevant first parameterization has already been inquired. A run is understood here as meaning running through steps d) to g) or running once through steps h) to j). With a negative classification, the control software may determine in step j) the recognition probability for the adapted first parameterization as 0%, provided that the relevant first parameterization was inquired for the first time, or for example an average value of 0% and the recognition probability already determined in a previous run in step j) or already in step g) for the same first parameterization, provided that the relevant first parameterization has already been inquired. The averaging may take place in each case in such a way that each inquiry of the parameter value is given the same weighting.

The recognition probability is typically determined in step j) as the value of the recognition probability function for the first parameterization adapted in step h) on the basis of the classification of the adapted stimulus image. For this purpose, the recognition probability function may be adapted to the recognition probability determined for the first parameterization (for example the 0% or 100% from the previous example) by fitting. The recognition probability function is typically a sigmoid function fitted to the recognition probability determined for the adapted first parameterization as well as to recognition probabilities possibly determined in previous runs in step j) or in step g) for the respective first parameterizations. The value assigned by the fitted recognition probability function to the first parameterization is typically used as the recognition probability for the first parameterization for the further course of the method according to the disclosure.

In step k), the control software (in particular the psychophysical algorithm) typically checks whether a termination criterion has been achieved. If a termination criterion has been achieved, the control software carries out step l). If no termination criterion has been achieved, steps h) to k) are repeated again. The psychophysical algorithm carries out a recursion until the threshold of the subjective visual acuity is found, that is to say until the first parameterization (in particular the image size) has come sufficiently close to the threshold and/or has reached the threshold, so that subsequently in step l) the threshold can be determined.

When steps h) to j) are repeated for the last time according to step k), in certain embodiments of the disclosure termination may already take place after step h) or i). Depending on the embodiment, in the last repetition, adapting the first parameterization of the stimulus image may already be sufficient for determining the threshold in step l) (see below). Carrying out steps i) and/or j) is therefore optional in the last repetition.

The psychophysical algorithm that is typically used may proceed on the basis of an adaptive step method. Suitable examples of the adaptive step method are BestPEST, PSI, the up-down staircase method and the constant-stimuli method. Depending on the method used, the procedure for determining the threshold of the subjective visual acuity according to step l) may differ. For example, the threshold of the subjective visual acuity (such as for example in the up-down staircase method) may be determined by averaging the values of the first parameterization achieved at a number of reversal points. Reversal points (or local extrema) are understood here as meaning points in a graphical plot of the first parameterization over the consecutive number of runs at which the adaptation changes from smaller to larger first parameterizations or from larger to smaller first parameterizations. A run is understood as meaning running through steps d) to g) or running once through steps h) to j). With other adaptive step methods (for example BestPEST), the value of the threshold may be determined as the first parameterization to which the recognition probability function assigns the recognition probability 50% after the termination criterion has been achieved. The recognition probability function is in this case typically obtained as a fit to the recognition probabilities determined in the individual runs in steps j) or in step g) for the respective first parameterizations.

The control software (typically the psychophysical algorithm) typically works with a manifestation of a feature that changes randomly each time steps h-j are run through, for example in the case of a Landolt ring with a randomly changing gap alignment.

In step l), the threshold of the subjective visual acuity is typically determined on the basis of the recognition probabilities determined for the respective first parameterizations of the stimulus image. Various embodiments are possible for this. For example, the first parameterization achieved the last time steps h) to j) are run through may be adopted as the value of the threshold of the subjective visual acuity. In this case, steps i) and/or j) could thus be dispensed with in the last run. The value of the threshold of the subjective visual acuity is typically determined as the first parameterization to which the recognition probability function assigns the recognition probability 50% after the termination criterion has been achieved. The recognition probability function is typically obtained as a fit to the recognition probabilities determined in the individual runs in steps j) or in step g) for the respective first parameterizations.

According to step m), steps d) to l) are run through sequentially a number of times. The individual steps are in this case typically run through in the specified order.

According to step m), the at least one property of the optical aid, in particular of the spectacle lens, is typically varied from run to run. The at least one property is therefore manifested to different degrees each time steps d) to l) are run through. This allows a comparison to be made between different values of the property, for example between different refractive powers of a spectacle lens. The refractive power is an example of a property of the optical aid (in particular the spectacle lens) that is applied to the stimulus image to produce a second parameterization. In this case, a sharpness of the stimulus image corresponds to the refractive power as a second parameterization. The refractive power of the optimized optical aid (in particular spectacle lens) selected in step n) therefore corresponds here to the sharpness (second parameterization) of the stimulus image of maximum sharpness.

The optical aid (in particular spectacle lens) selected in step n) is specifically optimized for the person's eye.

The term "highest subjective visual acuity" (or synonymously "highest subjective visual performance value") stands for the lowest or highest (depending on the type of parameter) position of the threshold of the subjective visual acuity. Depending on the type of parameter, this may be the highest or the lowest first parameterization with which recognition is still possible for example with 50% recognition probability. In the case of the image size as the first parameter, the highest subjective visual acuity is obtained for example for the configuration of the optical aid (in particular the spectacle lens) with which the lowest threshold was determined in step l). For this configuration of the optical aid, the lowest value for the image size is therefore required for recognition. This configuration of the optical aid therefore allows the highest resolution for the person's eye.

With the method according to the disclosure, an optical aid optimized for a certain person (in particular a spectacle lens optimized for the certain person) can be provided without any further action by the person. In particular, the person does not have to undergo laborious examinations with a large number of differently designed optical aids (in particular with a large number of differently designed spectacle lenses). This avoids disruptive influences, for example due to fatigue. In addition, no modeling of filter functions is required. Furthermore, when using the method according to the disclosure, it is not necessary to manufacture the large number of differently designed optical aids (in particular spectacle lenses). With the aid of the method according to the disclosure, the subjective visual acuity of the person can be determined quickly, without disruptive influences and with good accuracy. The effect of a large number of differently designed optical aids (in particular spectacle lenses) on the subjective visual acuity of the person can be compared inexpensively and quickly, and consequently a property of the optical aid (in particular spectacle lenses) optimized for this person can be selected inexpensively and quickly. In addition, the method according to the disclosure can also be used for combinations of different optical aberrations. For example, different combinations of astigmatism and defocus can be compared and an optimal combination thereof can be selected.

According to an exemplary embodiment of the disclosure, it is provided that the termination criterion comprises one or more of the following criteria:

reaching a predetermined number of repetitions of running through steps h) to j) according to step k), reaching a predetermined number of times a difference between successive adapted first parameterizations when repeatedly running through steps h) to j) according to step k) undershoots a predetermined limit value, and reaching a predetermined number of reversals.

Depending on the predetermined number, according to the second criterion mentioned here, undershooting once may be sufficient to meet the termination criterion (the predetermined number is equal to 1) or undershooting twice or more frequently may be required to meet the termination criterion. This criterion therefore describes a (sufficient) convergence of the first parameterization with the threshold of the subjective visual acuity. The "difference between successive adapted first parameterizations . . . when repeatedly running through steps h) to j) according to step k)" is for example a difference between image sizes adapted in successive runs in step h) or viewing angles ($\Delta\alpha_v$) corresponding to the adapted image sizes. The amount of the difference is decisive. It is therefore irrelevant whether the convergence is toward larger values of the first parameterization or toward smaller values of the first parameterization.

"Reversals" stand for the reversal points (or local extrema) already described above in a sequence of the first parameterization adapted according to step h) when repeating steps h) to j) according to step k). The term "reversal" could therefore also be replaced by the term "reversal point". A "reversal" can also be defined as a change between positive and negative classification in step i), that is to say between the classifications "recognized" and "not recognized", in the sequence of the adapted first parameterization when repeating steps h) to j) according to step k). The predetermined number of reversals therefore stands for a jumping back and forth (in particular multiple times) between positive and negative classification or between negative and positive classification. The reaching of a sufficiently high number (that is to say in particular the predetermined number) of reversals is an indication that the first parameterization is fluctuating precisely around the value of the threshold. This means that the value of the threshold lies exactly between the first parameterizations achieved at the reversal points. The value of the threshold is typically determined as the average value of the first parameterizations achieved at the reversal points.

The procedure for determining the value of the threshold typically depends on the type of termination criterion. When the predetermined number of repetitions of running through steps h) to j) is reached as the termination criterion, the first parameterization achieved during the last run may be adopted for example as the value of the threshold. In this case, steps i) and j) could thus be dispensed with in the last run. The value of the threshold is typically determined as the first parameterization to which the recognition probability function assigns the recognition probability 50% after the termination criterion has been achieved. The recognition probability function is typically obtained as a fit to the recognition probabilities determined in the individual runs in steps j) or in step g) for the respective first parameterizations.

According to a further exemplary embodiment of the disclosure, it is provided that the second parameterization performed when parameterizing the stimulus image in accordance with step d) comprises applying at least one property of a person's eye, in particular an optical aberration of the person's eye, to the stimulus image.

As already explained above, the optimization of an optical aid (in particular a spectacle lens) according to the disclosure is carried out specifically for an eye of a certain person. Thanks to the method according to the disclosure, it is not necessary that the person must endure laborious subjective measurements.

The person is typically not among the real test subjects who contributed to the creation of the at least one training data set.

The second parameterization may therefore comprise the application of an optical aberration of the person's eye to the stimulus image. The second parameterization may also comprise the application of various optical aberrations of the person's eye to the stimulus image. The second parameterization may alternatively or additionally comprise the application of distortions and/or scotomas of the person's eye to the stimulus image.

According to a further exemplary embodiment of the disclosure, it is provided that the property of the optical aid applied to the stimulus image in accordance with step m) when parameterizing the stimulus image in accordance with step d) comprises an optical aberration of the optical aid. The optical aid is in this case typically a spectacle lens.

The second parameterization may therefore comprise the application of an optical aberration of the optical aid (in particular the spectacle lens) to the stimulus image. The second parameterization may also comprise the application of various optical aberrations of the optical aid (in particular the spectacle lens) to the stimulus image. The optical aberrations parameterized in the stimulus image when running through steps d) to l) may therefore result from the person's eye and/or from the optical aid. The second parameterization therefore typically relates to the entire optical system, that is to say to the eye and/or to an optical aid. The optical aid (for example the spectacle lens) typically brings about a correction, that is to say a compensation for defective vision of the eye. An optical aberration of the eye is in this case to be compensated for by a corresponding optical aberration on the optical aid. In this case, the optical aberration of the optical aid typically has the opposite sign to that of the optical aberration of the eye. For example, the optical aberration of the eye is +1 dpt defocus and the optical aberration of the optical aid is −1 dpt defocus.

According to a further exemplary embodiment of the disclosure, it is provided that the optical aberration of the person's eye is measured and/or calculated, and/or that the optical aberration of the optical aid is measured and/or calculated. It goes without saying that it may also be provided that a number of optical aberrations of the person's eye are measured and/or calculated, or that a number of optical aberrations of the optical aid are measured and/or calculated. The optical aid is typically a spectacle lens.

According to a further exemplary embodiment of the disclosure, it is provided that step c) comprises the provision of a feature space comprising a number of manifestations of a feature, that in step d) one of the manifestations of a feature is selected from the feature space and provided in the stimulus image before the parameterization of the stimulus image, and that in step h), before the adaptation of the first parameterization, one of the manifestations of a feature is again selected from the feature space and provided in the stimulus image.

The provision of the feature space therefore creates the possibility of selecting different manifestations of a feature. The feature space may be one-dimensional or multi-dimensional. If the stimulus image is a Landolt ring, the feature space comprises for example the eight possible alignments of the gap in the Landolt ring. In this example, in step d) one of the eight possible alignments of the gap is selected as a manifestation of a feature and provided in the stimulus image. Furthermore, in this example in step h) again one of the eight possible alignments of the gap is selected as a manifestation of a feature and provided in the stimulus image. The manifestation of a feature is typically selected randomly in each case, for example on the basis of a normal distribution or uniform distribution. In the case of a multi-dimensional feature space, the manifestation of a feature may be understood as a vector.

According to a further exemplary embodiment of the disclosure, it is provided that the neural network is a convolutional neural network.

A convolutional neural network (abbreviation CNN) stands for a neural network that has a network architecture with convolutional neurons. A convolutional neural network is particularly advantageous if intensity distributions are used, as when learning image contents.

According to a further exemplary embodiment of the disclosure, it is provided that steps b), c), d), e), g), h), j), k), l), m), and/or n) are carried out by control software. The control software may use a psychophysical algorithm. In this case, steps d), e), g), h), j), k) and/or l) are typically carried out by the psychophysical algorithm. Particularly typically, steps d), g), h), j), k) and l) are carried out by the psychophysical algorithm. In step e), the recognition probability function is typically provided to the psychophysical algorithm. Typically, the selection optionally performed in step d) of one of the manifestations of a feature from the feature space and provision in the stimulus image as well as the selection optionally performed again in step h) of one of the manifestations of a feature from the feature space and provision in the stimulus image are also carried out by the psychophysical algorithm. In addition, in steps f) and/or i), a positive or negative classification may be determined by the psychophysical algorithm.

Furthermore, the control software may comprise a number of parts, specifically training software, threshold determination software and/or optimization software. In step a), the at least one training data set is typically provided to the training software. Step b) is typically carried out by the training software. The threshold determination software is typically a psychophysical algorithm or the threshold determination software uses a psychophysical algorithm. Steps d), e), g), h), j), k) and/or l) are typically carried out by the psychophysical algorithm or by the threshold determination software. Particularly typically, steps d), g), h), j), k) and l) are carried out by the psychophysical algorithm or by the threshold determination software. In step e), the recognition probability function is typically provided by the optimization software to the psychophysical algorithm or to the threshold determination software. Typically, the selection optionally performed in step d) of one of the manifestations of a feature from the feature space and provision in the stimulus image as well as the selection optionally performed again in step h) of one of the manifestations of a feature from the feature space and provision in the stimulus image are also carried out by the psychophysical algorithm or by the threshold determination software. In addition, in steps f) and/or i), a positive or negative classification may be determined by the psychophysical algorithm or by the threshold determination software. Steps c), e), m) and/or n) are typically carried out by the optimization software.

As an alternative to this, the control software may be the psychophysical algorithm. In this case, steps d), e), g), h), j), k) and/or l) are carried out by the psychophysical algorithm, that is to say by the control software. In this case, steps d), g), h), j), k) and l) are typically carried out by the psychophysical algorithm, that is to say by the control software. The recognition probability function is typically provided to the psychophysical algorithm, that is to say to the control software, in step e). Typically, the selection optionally performed in step d) of one of the manifestations of a feature from the feature space and provision in the stimulus image as well as the selection optionally performed again in step h) of one of the manifestations of a feature from the feature space and provision in the stimulus image are also carried out by the psychophysical algorithm, that is to say by the control software. In addition, in steps f) and/or i), a positive or negative classification may be determined by the psychophysical algorithm.

The use of a psychophysical algorithm is advantageous because an efficient determination of the visual threshold is made possible by an adaptive gradation of the stimulus intensity (that is to say the first parameterization).

The control software may also comprise a number of psychophysical algorithms. The aim of the psychophysical algorithm is to determine the visual threshold of a specific visual task. Various methods of threshold determination are possible here.

According to a further exemplary embodiment of the disclosure, it is provided that the psychophysical algorithm proceeds on the basis of an adaptive step method. Examples of an adaptive step method are BestPEST, PSI, the up-down staircase method or the constant-stimuli method.

According to the disclosure, a method for producing an optical aid optimized according to the disclosure is also provided. The optical aid is in this case typically a spectacle lens. The production method comprises the following steps:

determining surface machining data according to the second parameterization of the optimized optical aid selected in step n), and feeding the surface machining data to an automatic machine for the machining of optical surfaces for performing the machining of the optical surfaces of blanks according to the surface machining data.

For example, the surface machining data are directed to the provision of a specific radius of an optical surface of a blank for producing the optimized optical aid. The automatic machine for the machining of optical surfaces carries out the machining on the blank according to the surface machining data. The automatic machine therefore provides for example the specific radius of an optical surface on the blank on the basis of the surface machining data and thereby produces the optimized optical aid.

According to a further exemplary embodiment of the disclosure, it is provided that the machining of the optical surfaces comprises grinding and/or polishing, the surface machining data comprise grinding data and/or polishing data and the automatic machine for the machining of optical surfaces comprises an automatic grinding and/or polishing machine.

According to the disclosure, an apparatus for producing optimized optical aids is also provided. The optical aids are in this case typically spectacle lenses. The apparatus according to the disclosure comprises an automatic machine for the machining of optical surfaces,
a device for determining surface machining data according to the second parameterization of the optimized optical aid selected in step n), and
an evaluation device for carrying out the optimization method according to the disclosure, comprising interfaces for reading in training data sets and for inputting and/or selecting stimulus images and parameterization data for the first and second parameterizations.

The automatic machine for the machining of optical surfaces is a conventional apparatus for the machining of optical surfaces (in particular of spectacle lenses). The machining of the optical surfaces takes place in this case in a manner known to the person skilled in the art.

The evaluation device may in this case comprise the device for determining surface machining data. The evaluation device and the device for determining surface machining data may alternatively be formed separately. An interface for transmitting the second parameterization of the optimized optical aid (typically the optimized spectacle lens) selected in step n) may be provided between the evaluation device and the device for determining surface machining data.

The evaluation device typically comprises one or more high-performance processors and/or clusters. As a result, the evaluation device can provide the high computing power required for training the neural network.

The apparatus according to the disclosure also typically comprises a test device for checking the machined optimized optical aids (typically the machined optimized spectacle lenses).

The optimization method according to the disclosure and/or any exemplary embodiments thereof described above can be computer-implemented. According to the disclosure, a computer program with program code that can be run on a processor for carrying out the method steps of the optimization method according to the disclosure and/or of any embodiments thereof described above is provided in particular. In particular, the computer program carries out the method steps of the method according to the disclosure by running through an algorithm.

For this purpose, the computer program is loaded on a computer or run on a computer. The evaluation device and/or the device for determining surface machining data may be designed as a computer or comprise a computer. Alternatively, the computer may comprise the evaluation device and/or the device for determining surface machining data. The computer typically has interfaces for operation by a user and/or for display on a display unit.

According to the disclosure, a non-transitory storage medium with a computer program according to the disclosure stored on it is also provided.

BRIEF DESCRIPTION OF THE DRAWINGS

The disclosure will now be described with reference to the drawings wherein.

DESCRIPTION OF EXEMPLARY EMBODIMENTS

Figure 1:
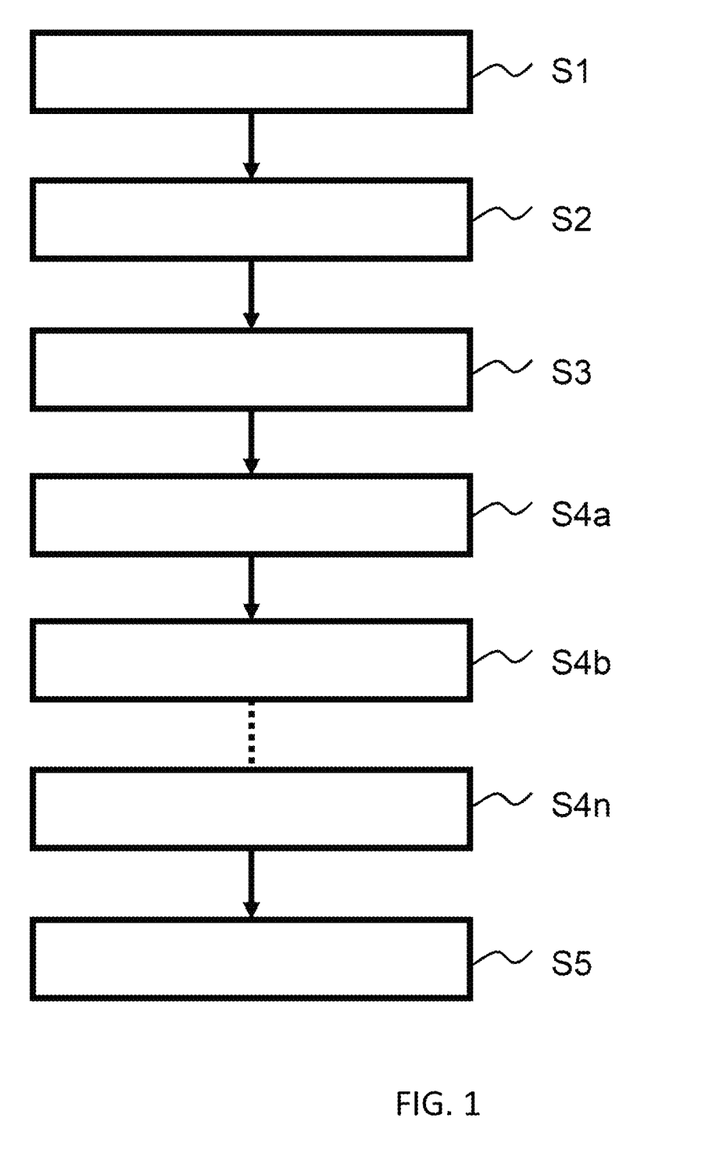
FIG. 1 shows a flow diagram for the sequence of an exemplary embodiment of a method according to the disclosure for optimizing an optical aid.

FIG. 1 shows a flow diagram for the sequence of an exemplary embodiment of a method according to the disclosure for optimizing an optical aid by means of automatic determination of subjective visual acuity. The optical aid is in this case specifically optimized for an eye of a person. The optical aid is for example a spectacle lens.

In a step S1, a training data set is provided. The training data set provided reflects the subjective visual acuity of a large number of real test subjects when recognizing stimulus images.

For example, a Landolt ring (or "Landolt C") is presented a number of times in each case to the real test subjects as a stimulus image on a monitor. The presentation is in each case carried out under standardized conditions; in particular, the distance between the monitor and the test subject is fixed. The gap of the Landolt ring may in this case have an alignment from eight possible angles, specifically "0°", "45°", "90°", "135°", "180°", "225°", "270°," or "315°". Each time the Landolt ring is presented, one of these gap alignments is selected at random. In addition, the Landolt ring has a different parameterization for each presentation. For example, the Landolt ring is gradually presented with different image sizes. Given the fixed distance between the monitor and the test subject, the image size corresponds here to a viewing angle. The real test subject has to communicate the gap alignments that he/she subjectively recognizes for each parameterization presented to him/her (that is to say here the image size or the viewing angle) of the Landolt ring. This subjective response of the real test subject may take place by actuating various keys The real test person has to definitively decide here on a specific gap alignment from the possible angles "0°", "45°", "90°", "135°", "180°", "225°", "270°," or "315°". Therefore, in the event that the real test person cannot recognize a gap alignment, he/she has to guess.

To create the training data set, with the large number of test subjects, for example altogether 2,500 presentations of a Landolt ring, in each case with a different image size, for each gap alignment are carried out. Given the eight different gap alignments of the Landolt ring, the number of presentations has to be multiplied by eight, and so is for example 20,000.

Furthermore, a number of runs is carried out for each individual real test subject. In this case, the stimulus images (that is to say the differently sized and differently aligned Landolt rings) have a differently manifested optical aberration, for example a different sharpness, in each run. For example, the Landolt ring may be presented with a certain sharpness, i.e., more or less sharp, in each of seven runs, the sharpness differing from run to run. This correspondingly results for example in a total number of seven times 20,000, therefore 140,000, presentations for the creation of a training data set.

The training data sets provided typically comprise the Landolt rings presented as stimulus images, the respective actual gap alignment of the presented Landolt rings and the respective subjective response of the test persons to the gap alignment of the presented Landolt rings.

In a step S2, an artificial neural network is trained by means of the training data set. The artificial neural network is for example a convolutional neural network (abbreviation CNN), that is to say a neural network that has a network architecture with convolutional neurons. The network architecture can have different numbers of convolutional layers. Different learning rates can be used.

In a step S3, a stimulus image is created generically. In the exemplary embodiment presented here, the Landolt ring is provided with eight different manifestations of a feature, specifically with its eight different gap alignments "0°," "45°," "90°," "135°," "180°," "225°," "270°," or "315°". The different manifestations of a feature (gap alignments) in this case form a feature space.

In a step S4a, the threshold of the subjective visual acuity is determined for a first optical system. The first optical system is for example the eye of a person without an optical aid (or with an optical aid without optical aberration). In a step S4b, the threshold of the subjective visual acuity is determined for a second optical system. The second optical system comprises the person's eye and a first optical aid. The first optical aid is typically a first spectacle lens, that is to say a spectacle lens with a first value of an optical aberration, for example a spectacle lens with a first refractive power. The refractive power is an example of a property of the spectacle lens (optical aid) that is applied to the stimulus image to produce a second parameterization. In the example considered here, a certain sharpness in the stimulus image is produced as a second parameterization. The sharpness results from a combination of the refractive power of the eye and of the spectacle lens (optical aid). The sharpness resulting in the stimulus image therefore corresponds to the refractive power of the entire optical system. In a step S4n, the threshold of the subjective visual acuity is determined for an nth optical system. The nth optical system comprises the person's eye and an $(n-1)^{th}$ optical aid, for example a spectacle lens with an $(n-1)^{th}$ refractive power. Altogether, the threshold of subjective visual acuity is therefore determined for n optical systems with in each case a different refractive power for the spectacle lens. In the case of the first optical system in the exemplary embodiment under consideration, the refractive power for the spectacle lens is equal to O.

In a step S5, the optical aid, that is to say in the example mentioned the spectacle lens, for which the highest subjective visual acuity was determined in steps 4a to 4n is selected. The spectacle lens selected here is specifically optimized for the person's eye. In the exemplary embodiment under consideration, the stimulus image with the highest sharpness results here from the combination of the refractive power of the eye with the refractive power of the optimized spectacle lens.

The "highest subjective visual acuity" stands for the lowest or highest position (depending on the type of parameter) of the threshold of the subjective visual acuity. In the case of the image size as the first parameter, the highest subjective visual acuity is obtained for the optical system from steps 4a to 4n for which the lowest threshold was determined. This optical system still allows the stimulus image (Landolt ring) to be recognized at the smallest image size compared with the other optical systems examined in steps 4a to 4n. The optical aid (in particular spectacle lens) provided in this optical system is therefore the optical aid (in particular spectacle lens) optimized for the person's eye. In combination with this optimized optical aid (in particular spectacle lens), the person's eye can therefore achieve the highest resolution.

Figure 2:
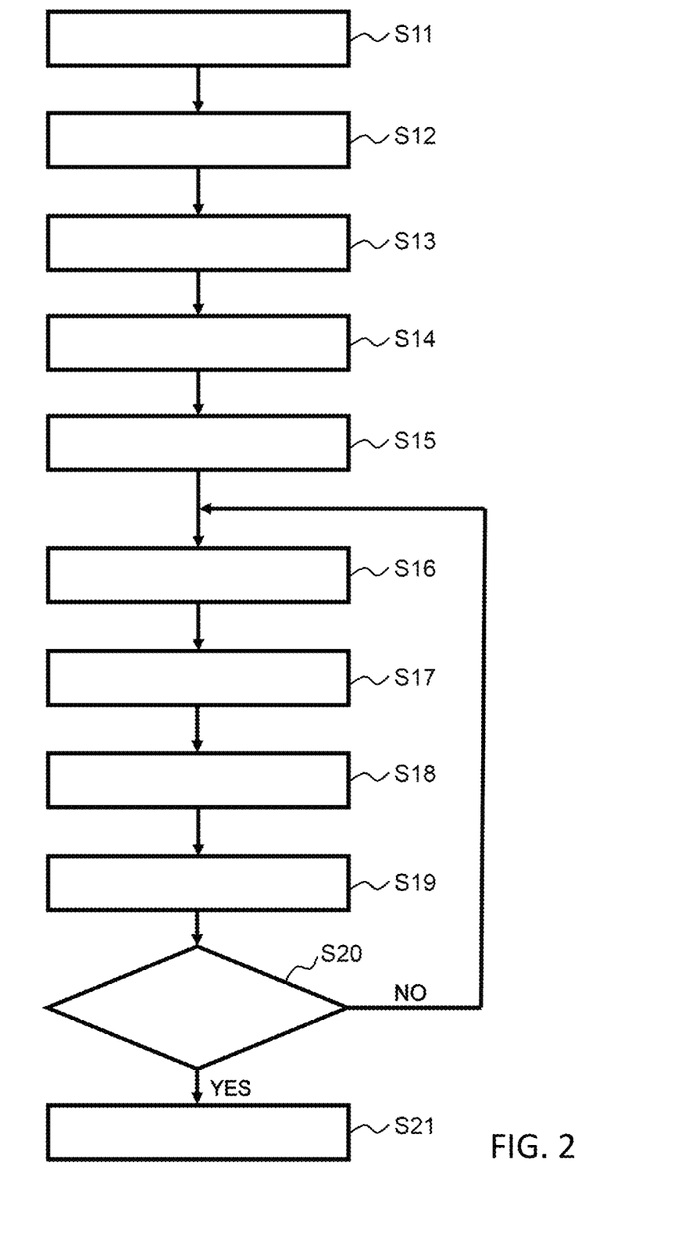
FIG. 2 shows a flow diagram for the sequence of a threshold determination method within the exemplary embodiment shown in FIG. 1.

FIG. 2 shows a flow diagram supplementing the exemplary embodiment of FIG. 1 for the sequence of the determination of the threshold of the subjective visual acuity performed in each case in steps 4a to 4n for the respectively considered optical system comprising the person's eye and the optical aid (in particular spectacle lens) differently designed in each case. The method for determining the threshold of the subjective visual acuity is also referred to below as the threshold determination method. The threshold determination method is carried out by control software using a psychophysical algorithm.

In a step S11, one of the possible manifestations of a feature is selected by the psychophysical algorithm. For this purpose, the feature space is typically fed to the psychophysical algorithm and a manifestation of a feature is selected from the feature space by the psychophysical algorithm by means of a random distribution. Depending on the nature of the feature space, a certain random distribution can be provided. In the example of a Landolt ring considered here, one of the eight possible alignments of the gap in the Landolt ring is therefore selected. A Landolt ring with this gap alignment is therefore provided. The selection takes place randomly, for example on the basis of a normal distribution or a uniform distribution.

In a step S12, the stimulus image (Landolt ring) is parameterized by the psychophysical algorithm. For this purpose, the psychophysical algorithm is typically fed a first and a second parameter space, and a first and a second parameterization are carried out by the psychophysical algorithm. The first and second parameterizations concern different parameters. In the exemplary embodiment considered here, the first parameterization of the stimulus image (Landolt ring) is carried out on the basis of the first parameter, image size. A specific value for the image size (also referred to in the following simply as "an image size") is therefore provided as a first parameterization. This image size is an initial value (input value) for the psychophysical algorithm. The image size corresponds to a viewing angle obtained from it under standard conditions. In the exemplary embodiment considered here, the second parameterization results from an optical aberration, in particular from a spherical defocus, of the respective optical system, that is to say the person's eye and/or the spectacle lens. A specific sharpness and/or a specific contrast in the stimulus image is obtained here as a second parameterization. The optical aberration, in particular the spherical defocus, of the spectacle lens to be optimized is varied over steps 4a to 4n. The second parameterization also varies accordingly over steps 4a to 4n. The stimulus image is typically provided in each of steps 4a to 4n with a different second parameterization, that is to say with a different sharpness and/or contrast value.

Figure 3B:
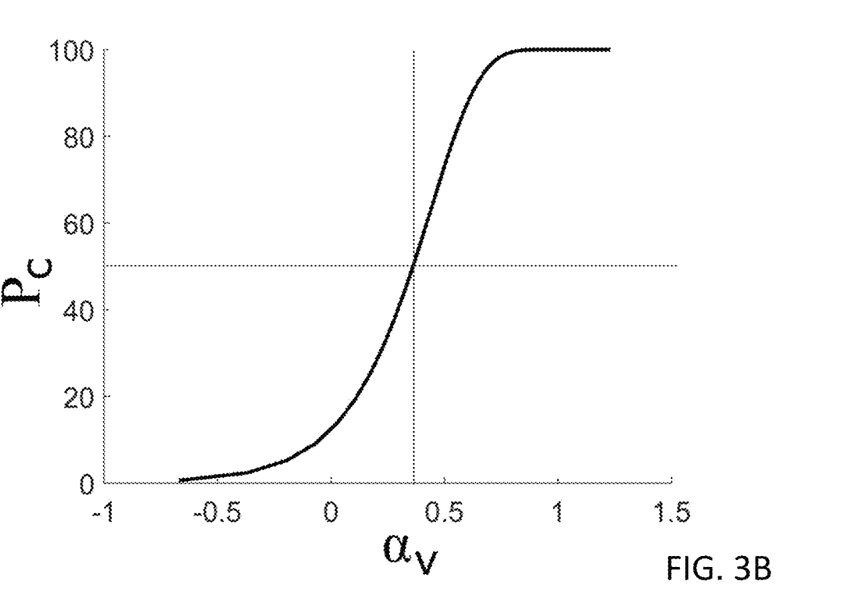
FIG. 3B shows a recognition probability function for the first optical aid.
Figure 4A:
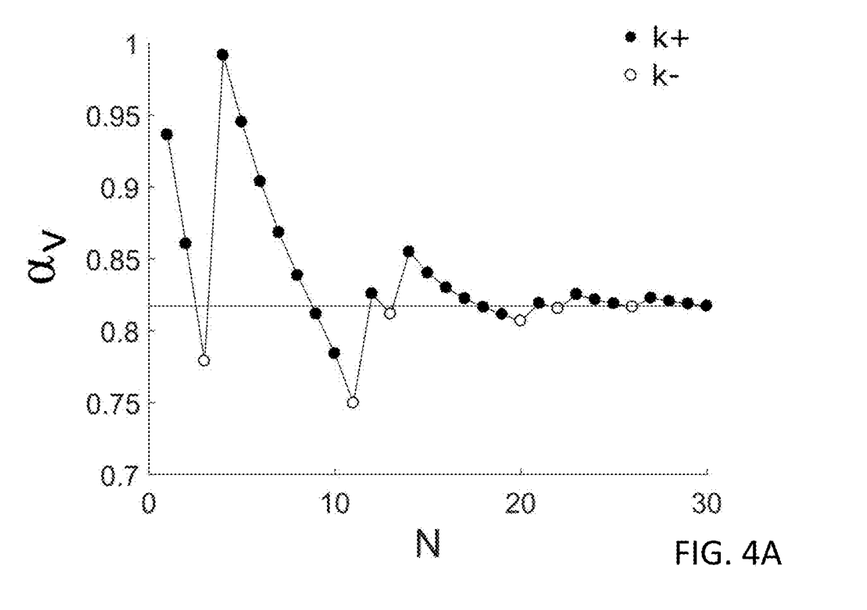
FIG. 4A shows a diagram for the sequence of a threshold determination method for a second optical aid.
Figure 4B:
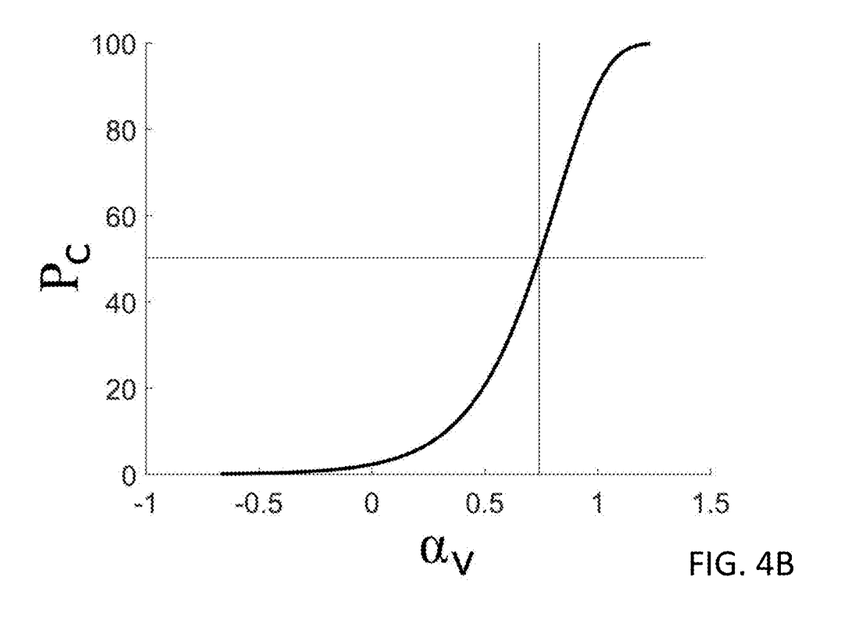
FIG. 4B shows a recognition probability function for the second optical aid.

In a step S13, the psychophysical algorithm is initialized. The aim of the psychophysical algorithm is to determine the visual threshold for the respectively considered optical system comprising the person's eye and/or the optical aid (in particular spectacle lens). In the exemplary embodiment considered here, the visual threshold relates to a minimum still recognizable image size or, corresponding thereto, to a minimum still recognizable viewing angle. The psychophysical algorithm is based here on an adaptive step method, for example BestPEST, an up-down staircase method or a constant-stimuli method. In the exemplary embodiment considered here, BestPEST is used. The initialization of the psychophysical algorithm stands for the beginning of the adaptive step method with the input values selected in step S12 for the first and second parameterizations. In step S13, a recognition probability function is also provided. The recognition probability function assigns a recognition probability $P_C$ to each first parameterization, that is to say to each image size. The recognition probability function is a sigmoid function. Examples of recognition probability functions are shown in FIGS. 3B and 4B.

In a step S14, the trained neural network classifies the stimulus image (the Landolt ring). Classifying the stimulus image is understood as meaning the assignment of the stimulus image to different categories, in the case of the Landolt ring considered here into the categories "0°," "45°," "90°," "135°," "180°," "225°," "270°," or "315°". The assignment made by the trained neural network is compared with the actual alignment of the gap in the Landolt ring. The neural network provides a classification of the stimulus image (Landolt ring). If the alignment of the gap in the Landolt ring is correctly determined by the neural network, the psychophysical algorithm determines the classification as positive. If the alignment of the gap in the Landolt ring is incorrectly determined by the neural network, the psychophysical algorithm determines the classification as negative.

In a step S15, the psychophysical algorithm determines a recognition probability $P_C$ as the value of the recognition probability function for the image size provided in step S12 on the basis of the classification from step S13. If the classification is positive, the control software (the psychophysical algorithm) determines the recognition probability $P_C$ for the relevant image size (first parameterization) as 100%. If the classification is negative, the control software (the psychophysical algorithm) determines the recognition probability $P_C$ for the relevant image size (first parameterization) as 0%. With BestPEST, the recognition probability function can be adapted to the recognition probability $P_C$ determined for the relevant image size by fitting. The recognition probability function is typically a fitted sigmoid function.

In a step S16, one of the possible manifestations of a feature is again selected by the psychophysical algorithm. The selection once again takes place randomly, for example on the basis of a normal distribution or a uniform distribution. In the example of a Landolt ring considered here, again one of the eight possible alignments of the gap in the Landolt ring is thus selected and a Landolt ring with this newly selected gap alignment is provided in the stimulus image. A Landolt ring with an unchanged gap alignment could still be provided coincidentally (with a probability of ⅛). As an alternative to this, it may also be provided that one of the eight possible alignments of the gap in the Landolt ring is selected at random until a gap alignment that has changed compared to the previously selected gap alignment is selected.

In a step S17, the psychophysical algorithm adapts the first parameterization of the stimulus image (that is to say the image size of the Landolt ring) on the basis of the recognition probability $P_C$ assigned by the recognition probability function. With a recognition probability of over 50% (or of at least 50%), the image size is typically adapted in such a way that recognition of the gap alignment in the Landolt ring with the new image size becomes more difficult, the image size is therefore reduced. Correspondingly, with a recognition probability of below 50%, the image size may be adapted in such a way that recognition of the gap alignment in the Landolt ring becomes easier with the new image size, the image size is therefore increased. Furthermore, the amount of the difference between the new image size and the previous image size in the exemplary embodiment considered here (BestPEST) is also dependent on the recognition probability assigned by the recognition probability function. The amount of this difference is typically all the smaller, the closer the assigned recognition probability is to 50%. The aim of adapting the image size is to bring the image size close to the visual threshold.

Depending on the type of psychophysical algorithm typically used, it may be provided that, when adapting the image size (first parameterization) in step S17, an image size that was not previously set (for example BestPEST) is always set, or that an already previously used image size may be set again in step S17 (for example the up-down-staircase method, constant-stimuli method). Correspondingly, depending on the type of psychophysical algorithm, a certain first parameterization may be inquired only once or a number of times.

In a step S18, the trained neural network classifies the adapted stimulus image (Landolt ring). The procedure is as in step S14. The neural network again provides a classification of the stimulus image (Landolt ring). If the alignment of the gap in the Landolt ring is correctly determined, the classification is positive. If the alignment of the gap in the Landolt ring is incorrectly determined, the classification is negative.

In a step S19, the psychophysical algorithm determines the recognition probability $P_C$ as the value of the recognition probability function for the image size adjusted in step S17 on the basis of the classification from step S18. In this case, the psychophysical algorithm determines the recognition probability $P_C$ for the adjusted image size with a positive classification as 100% and with a negative classification as 0%. In the exemplary embodiment considered here (Best-PEST), the image size is adjusted in very fine increments. Therefore, BestPEST does not normally inquire a certain image size repeatedly. In the case of other adaptive step methods or, as an exception, with BestPEST, when there is a positive classification, an average value of 100% and the recognition probability already previously determined (in a previous run in step S19 or already in step S15) for the same image size may be determined by the psychophysical algorithm, as long as the relevant image size has already been inquired. When there is a negative classification, as long as the relevant image size has already been inquired, the psychophysical algorithm may determine the recognition probability $P_C$ for the adjusted image size as a mean of 0% and the recognition probability already determined before (in a previous run in step S19 or already in step S15) for the same image size. The averaging may then take place in each case in such a way that each inquiry of the relevant image size is given the same weighting. With BestPEST, typically only the recognition probabilities $P_C$ equal to 0% or 100% are possible when inquiring a specific image size (first parameterization). With BestPEST, the recognition probability function can be adapted to the recognition probability determined for the adjusted image size by fitting. The recognition probability function is typically a sigmoid function fitted to the recognition probability determined for the adapted image size and to recognition probabilities determined for the respective image sizes in previous runs in step S19 or in step S15 (see FIGS. 3B and 4B).

In a step S20, the psychophysical algorithm checks whether a termination criterion has been achieved. If a termination criterion has been achieved, a step S21 follows (see below). If no termination criterion has been achieved, steps S16 to S20 are repeated again. The psychophysical algorithm thereby provides any gap alignment of the Landolt ring each time step S16 is run through. The psychophysical algorithm carries out a recursion until the threshold of the subjective visual acuity is found, that is to say until the first parameterization (the image size) has come sufficiently close to the threshold and/or has reached the threshold, so that subsequently (in step S21) the threshold can be determined.

In the exemplary embodiment considered here, the termination criterion is achieved by one of the following cases:
  reaching a predetermined number of repetitions of running through steps S16 bis S19. For this purpose, a counter which is for example incremented by 1 in step S16 may be provided.
  reaching a predetermined number of times a difference between successive adapted first parameterizations (image sizes) when repeatedly running through step S17 undershoots a predetermined limit value. In this case, the predetermined number may for example be equal to three, so that it is necessary to undershoot three times in order to meet the termination criterion. This criterion therefore describes a (sufficient) convergence of the first parameterization (image size) with the threshold of the subjective visual acuity. In the exemplary embodiment under consideration, the difference is formed from image sizes adapted in successive runs of step S17 or viewing angles ($\Delta\alpha_v$) corresponding to the adapted image sizes. The amount of the difference is decisive here. It is therefore irrelevant whether the convergence is toward larger values of the image size or the viewing angle ($\Delta\alpha_v$) or toward smaller values of the image size or the viewing angle (AO.
  reaching a predetermined number of reversals. "Reversals" stand for the reversal points (or local extrema) shown in FIGS. 3A and 4A in a sequence of the image size adapted according to step S17 when repeating steps S16 to S20. A "reversal" can therefore also be defined as a change between positive and negative classification (see step S14 or S18) in the sequence of FIG. 3A or 4A. A "reversal" is therefore a jumping back and forth between positive and negative classification or between negative and positive classification. The reaching of a sufficiently high number (that is to say in particular the predetermined number) of reversals is an indication that the first parameterization (image size) is fluctuating precisely around the value of the threshold. This means that the value of the threshold lies exactly between the image sizes achieved at the reversal points.

In step S21, the psychophysical algorithm determines the threshold of the subjective visual acuity on the basis of the recognition probabilities determined for the respective first parameterizations (image sizes) of the stimulus image. Depending on the type of adaptive step method used, the procedure for determining the threshold of subjective visual acuity may differ. In the case of a predetermined number of repetitions of steps S16 to S19, with BestPEST, for example the adjusted image size (first parameterization) obtained during the last execution of step S17 may be adopted as the threshold. As an alternative to this, with BestPEST, the image size (first parameterization) for which the fitted recognition probability function gives the recognition probability 50% may also be determined as the threshold.

Figure 3A:
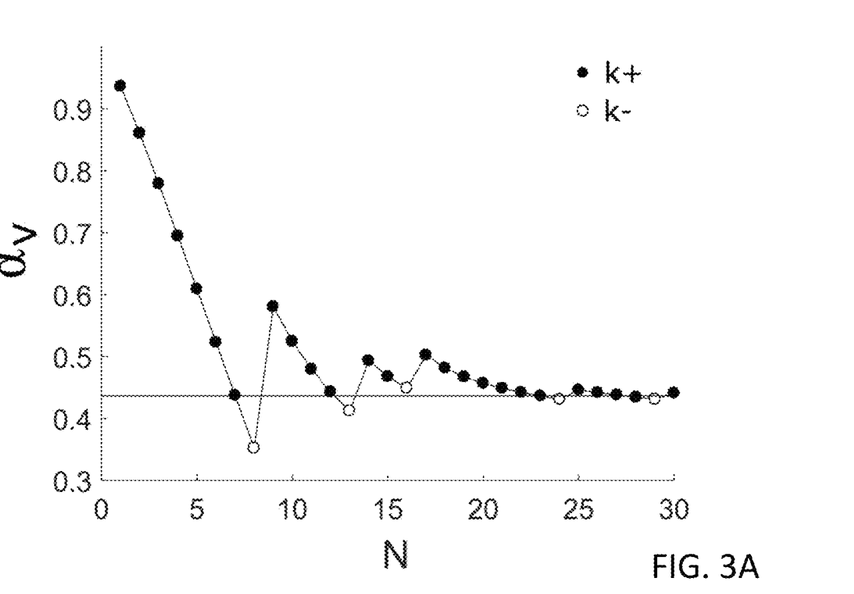
FIG. 3A shows a diagram for the sequence of a threshold determination method for a first optical aid.

FIG. 3A shows a diagram for the sequence of a threshold determination method for a first optical aid. In the exemplary embodiment considered here, the first optical aid is a first spectacle lens or a spectacle lens with a first refractive power. FIG. 4A shows a diagram for the sequence of a threshold determination method for a second optical aid. In the exemplary embodiment considered here, the second optical aid is a second spectacle lens or a spectacle lens with a second refractive power. The term "diagram for the sequence of a threshold determination method" is referred to below as the threshold determination diagram for short.

In the two threshold determination diagrams, the consecutive number of runs N of the threshold determination method is in each case plotted to the right. The first run (N=1) relates here to running through steps S11 to S15, the following runs in each case to running through steps S16 to S20 according to FIG. 2. The two threshold determination diagrams respectively show a graphical plot of the first parameterization over the consecutive number of runs N. In the exemplary embodiment considered here, the first parameterization is the image size or the corresponding viewing angle $\alpha_v$. The inquired viewing angle $\alpha_v$ is shown for each run N. The viewing angle $\alpha_v$ for the case of a positive classification k+ by the trained neural network is depicted here as a filled circular disk and for the case of a negative classification k− by the trained neural network as a circular ring.

FIG. 3B shows a recognition probability function for the first optical aid, that is to say for the first spectacle lens or for the spectacle lens with the first refractive power. FIG. 4B shows a recognition probability function for the second optical aid, that is to say for the second spectacle lens or for the spectacle lens with a second refractive power. In this case, a recognition probability $P_C$ is respectively plotted against the viewing angle $\alpha_v$. For each viewing angle $\alpha_v$, the psychophysical algorithm determines a recognition probability $P_C$ by fitting a sigmoid function to the recognition probabilities determined in step S15 for the input image size and in each case in step S19 for the respective adapted image sizes. Since the recognition probabilities determined in step S15 for the input image size and in each case in step S19 for the respective adapted image sizes only have the values 0% or 100% in the case of BestPEST, these recognition probabilities are not shown in FIGS. 3B and 4B.

In the exemplary embodiment considered here, BestPEST is used as the adaptive step method. If the recognition probability function assigns a recognition probability $P_C$ of at least 50% to a viewing angle $\alpha_v$, the viewing angle $\alpha_v$ is reduced in the subsequent run (N+1) during the adaptation in step S17. The amount of the reduction in the viewing angle, that is to say the amount of the viewing angle difference $\Delta\alpha_v$, also depends here on the assigned recognition probability $P_C$. It is typically all the lower, the closer the recognition probability $P_C$ is to 50%. If the recognition probability function assigns a recognition probability $P_C$ of less than 50% to a viewing angle $\alpha_v$, the viewing angle $\alpha_v$ is increased in the subsequent run (N+1) during the adaptation in step S17. The amount of the increase in the viewing angle, that is to say the amount of the viewing angle difference $\Delta\alpha_v$, also depends here on the recognition probability $P_C$ assigned by the recognition probability function. It is typically all the lower, the closer the recognition probability $P_C$ is to 50%. After reaching a predetermined number of runs N, in the exemplary embodiment under consideration here N=30, the inquiry of further viewing angles $\alpha_v$ is terminated.

The viewing angle $\alpha_v$ for which a recognition probability $P_C$ of 50% is achieved is determined as the value of the threshold. The value of the threshold is thus obtained graphically in FIGS. 3B and 4B by projecting the 50% line onto the right-hand axis by means of a vertical line drawn in each case. The threshold determined in this way is depicted in FIGS. 3A and 4A as a horizontal line.

In the exemplary embodiment considered here, a lower value for the threshold is obtained for the spectacle lens with the first refractive power (FIGS. 3A and 3B) than for the spectacle lens with the second refractive power (FIGS. 4A and 4B). The spectacle lens with the first refractive power therefore still allows the person's eye to recognize image sizes (or viewing angles) that can no longer be recognized with the spectacle lens with the second refractive power. The spectacle lens with the first refractive index therefore offers higher resolution specifically for the person. If only these two spectacle lenses have been subjected to the optimization process (see FIG. 1), the spectacle lens with the first refractive power is therefore selected as the spectacle lens optimized for the person's eye in step S5 of the optimization process.

Figure 5:
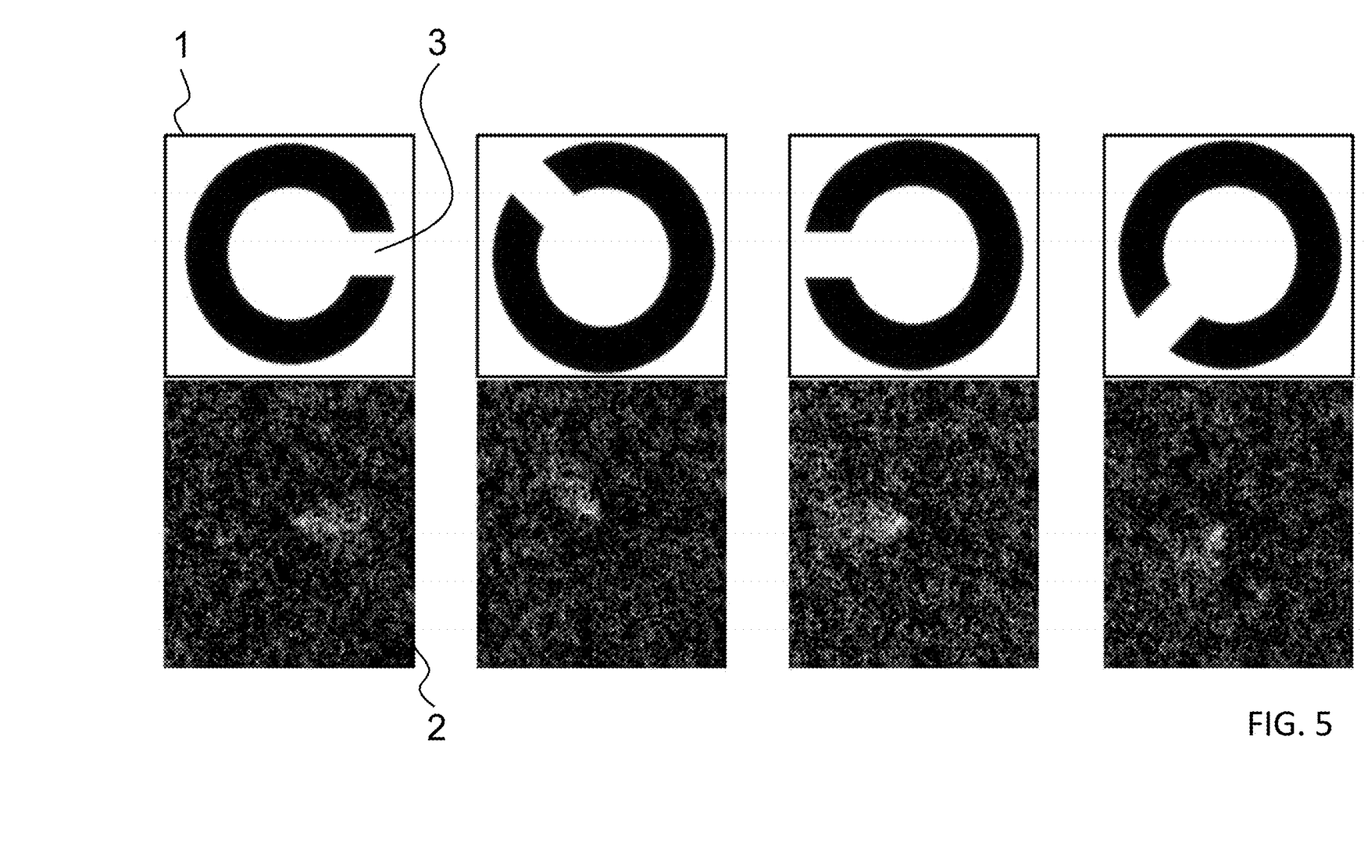
FIG. 5 shows a comparison of stimulus images and respectively associated visualization of learned weights of a trained neural network.

FIG. 5 shows a comparison of stimulus images 1 and respectively associated visualization 2 of learned weights of a trained neural network. FIG. 5 therefore shows the result of training the neural network. In this example, the neural network is a convolutional neural network. The stimulus images 1 are in each case a Landolt ring with the same image size (first parameterization) and the same sharpness (second parameterization). The stimulus images shown differ in the alignment of the gap 3 of the Landolt ring, that is to say in the manifestation of a feature. In the case of the first Landolt ring shown, the gap 3 is at 0°, in the case of the second shown Landolt ring at 135°, in the case of the third shown Landolt ring at 180° and in the case of the fourth shown Landolt ring at 225°. The other possible manifestations of the feature of the Landolt ring (gap alignments 45°, 90°, 270°, and 315°) are not considered in FIG. 5 for the purpose of better clarity. The visualization 2 for the gap alignment 0° shows for example a representation of all of the weights of the trained neural network that correspond to the gap alignment 0°. Also for the further manifestations of the feature (gap alignments), the representations of the weights of the trained neural network respectively corresponding to these manifestations of the feature are shown as a visualization 2. In the example shown, the stimulus images 1 and the associated visualizations 2 have in each case 500×500 pixels.

LIST OF REFERENCE SIGNS

1 Stimulus images
2 Visualization
3 Gap
$\alpha_v$ Viewing angle
$\Delta\alpha_v$ Viewing angle difference
k+ Positive classification
k− Negative classification
N Run
$P_C$ Recognition probability

The invention claimed is:

1. A method for optimizing an optical aid by automatic determination of a subjective visual acuity employing machine learning, the method comprising the following steps:
   a) providing at least one training data set;
   b) training an artificial neural network with the at least one training data set;
   c) generically creating a stimulus image;
   d) parameterizing the stimulus image in a first parameterization and a second parameterization;
   e) providing a recognition probability function;
   f) classifying the stimulus image by the trained neural network to provide a classification of the stimulus image;
   g) determining a recognition probability for the first parameterization performed in step d) on a basis of the classification of the stimulus image;
   h) adapting the first parameterization of the stimulus image on a basis of the determined recognition probability;
   i) classifying the adapted stimulus image by the trained neural network to provide a classification of the adapted stimulus image;
   j) determining the recognition probability for the first parameterization adapted in step h) on a basis of the classification of the adapted stimulus image;
   k) repeating steps h) to j) until a termination criterion is achieved to find a threshold for subjective visual acuity;
   l) determining the threshold of subjective visual acuity;
   m) repeatedly running through steps d) to l) with the second parameterization in each case, the second parameterization of the stimulus image in each case comprising the application of at least one property of the optical aid to the stimulus image; and
   n) optimizing the optical aid by selecting the second parameterization with a highest subjective visual acuity determined in step l).

2. The method as claimed in claim 1, wherein the termination criterion comprises one or more of the following criteria:
reaching a predetermined number of repetitions of running through steps h) to j) according to step k);
reaching a predetermined number of times a difference between successive adapted first parameterizations when repeatedly running through steps h) to j) according to step k) undershoots a predetermined limit value; and
reaching a predetermined number of reversals.

3. The method as claimed in claim 1, wherein the second parameterization performed when parameterizing the stimulus image in accordance with step d) comprises applying at least one property of a person's eye.

4. The method as claimed in claim 3, wherein the at least one property of the person's eye is an optical aberration of the person's eye.

5. The method as claimed in claim 1, wherein the property of the optical aid applied to the stimulus image in accordance with step m) when parameterizing the stimulus image in accordance with step d) comprises an optical aberration of the optical aid.

6. The method as claimed in claim 5, wherein at least one of the optical aberration of the person's eye is measured, calculated, or measured and calculated; and the optical aberration of the optical aid is measured, calculated, or measured and calculated.

7. The method as claimed in claim 1, wherein step c) comprises a provision of a feature space including a plurality of manifestations of a feature,
wherein in step d) one of the plurality of manifestations of the feature is selected from the feature space and provided in the stimulus image before the parameterization of the stimulus image, and
wherein in step h), before the adaptation of the first parameterization, the one of the plurality of manifestations of the feature is again selected from the feature space and provided in the stimulus image.

8. The method as claimed in claim 1, wherein the neural network is a convolutional neural network.

9. The method as claimed in claim 1, wherein at least one of steps b), c), d), e), g), h), j), k), l), m) and n) is carried out by control software.

10. The method as claimed in claim 9, wherein the control software employs a psychophysical algorithm or is the psychophysical algorithm.

11. The method as claimed in claim 8, wherein the control software employs a psychophysical algorithm or is the psychophysical algorithm, and wherein the psychophysical algorithm proceeds according to an adaptive step method.

12. A method for producing an optical aid optimized by a method as claimed in claim 1, the method comprising:
determining surface machining data according to the second parameterization of the optimized optical aid selected in step n); and
feeding the surface machining data to an automatic machine configured to machine optical surfaces to perform the machining of the optical surfaces of blanks according to the surface machining data.

13. The method as claimed in claim 10, wherein the machining of the optical surfaces comprises grinding, polishing, or grinding and polishing, the surface machining data comprise grinding data, polishing data, or the grinding data and the polishing data and the automatic machine configured to machine optical surfaces includes at least one of an automatic grinding machine or a polishing machine.

14. The method as claimed in claim 1, wherein the first parameterization of the stimulus image includes at least one of an image size of the stimulus image, a stimulus contrast, and a stimulus shape.

15. An apparatus for producing optimized optical aids, the apparatus comprising:
an automatic machine configured to machine optical surfaces;
an evaluation device configured to carry out the method as claimed in claim 1, the evaluation device including an interface configured to read in training data sets and to input, select, or input and select stimulus images and parameterization data for the first parameterization and the second parameterization; and
a device configured to determine surface machining data according to the second parameterization of the optimized optical aid selected in step n).

16. The apparatus as claimed in claim 15, further comprising a test device configured to check the processed optimized optical aids.

17. A computer program stored on a non-transitory storage medium and having program code to be run on a processor for carrying out the method steps of the method as claimed in claim 1.

18. The non-transitory storage medium with the computer program as claimed in claim 17 stored thereon.

* * * * *